(12) United States Patent
Cox (10) Patent No.: US 8,313,451 B2
(45) Date of Patent: Nov. 20, 2012

(54) ORTHOTIC DEVICE WITH SLIDING MECHANISM

(76) Inventor: William J. Cox, Fresno, CA (US)

( * ) Notice: Subject to any disclaimer, the term of this patent is extended or adjusted under 35 U.S.C. 154(b) by 439 days.

(21) Appl. No.: 12/583,948

(22) Filed: Aug. 27, 2009

(65) Prior Publication Data

US 2010/0069807 A1    Mar. 18, 2010

Related U.S. Application Data

(60) Provisional application No. 61/192,253, filed on Sep. 17, 2008.

(51) Int. Cl.
*A61F 5/00*    (2006.01)
(52) U.S. Cl. .......................................... 602/23
(58) Field of Classification Search .............. 602/23, 602/27, 28, 29; 36/109, 113, 140, 155, 156, 36/161, 173; D24/190, 192
See application file for complete search history.

(56) References Cited

U.S. PATENT DOCUMENTS

| | | | | |
|---|---|---|---|---|
| 4,530,173 A | * | 7/1985 | Jesinsky, Jr. | 36/92 |
| 4,719,926 A | * | 1/1988 | Nelson | 602/27 |
| 5,094,232 A | * | 3/1992 | Harris et al. | 602/16 |
| 5,183,036 A | * | 2/1993 | Spademan | 602/10 |
| 5,792,087 A | * | 8/1998 | Pringle | 602/27 |
| 5,865,778 A | * | 2/1999 | Johnson | 602/27 |
| 6,792,700 B2 | | 9/2004 | Gallegos | |
| 6,955,654 B2 | * | 10/2005 | Gilmour | 602/16 |
| 7,192,408 B2 | * | 3/2007 | Win | 602/16 |
| 7,294,114 B1 | | 11/2007 | Clement et al. | |
| 2002/0029009 A1 | * | 3/2002 | Bowman | 602/27 |
| 2003/0115775 A1 | * | 6/2003 | Mazzarolo | 36/89 |
| 2005/0131324 A1 | * | 6/2005 | Bledsoe | 602/23 |
| 2007/0289163 A1 | * | 12/2007 | Weiss | 36/44 |

* cited by examiner

*Primary Examiner* — Patricia Bianco
*Assistant Examiner* — Raymond E Harris
(74) *Attorney, Agent, or Firm* — Lumen Patent Firm (57) ABSTRACT

An orthotic foot device with a walking boot is provided. The orthotic foot device with a walking boot includes at least one boot wall having at least one guide disposed along an anteroposterior direction of the boot wall. At least one upright bar is disposed to attach to an individual's lower leg and is disposed to translatably engage the at least one guide. At least one fastener fixedly holds the at least one upright bar to the at least one guide when the at least one upright bar is desirably positioned the anatomical ankle axis and calf midline of a patient suffering from an injured Achilles tendon, hair line fractures of the foot and ankle, plantar fasciitis, diabetes, or other foot and ankle pathologies that require a cam boot.

15 Claims, 6 Drawing Sheets

ORTHOTIC DEVICE WITH SLIDING MECHANISM

CROSS-REFERENCE TO RELATED APPLICATIONS

This application is cross-referenced to and claims the benefit from U.S. Provisional Application 61/192,253 filed Sep. 17, 2008, and which are hereby incorporated by reference.

FIELD OF THE INVENTION

The invention relates to orthotic devices. In particular, the invention relates to orthotic foot devices where the walking boot of the device is capable of moving with respect to the uprights of the device.

BACKGROUND

Damage to the Achilles tendon is a common condition. This typically occurs while playing sports, exertion without proper stretching and warm up or stumbling while walking. Damage occurs due to a rapid contraction of the muscle causing the tendon to tear. An injured individual will feel pain near the back of the calf muscle and find it painful to walk, where the leg is significantly weakened.

Following the tendon repair, activity is not permitted for up to a few weeks and then the patient is fitted with a removable boot. Achilles injuries require the footwear to have important aspects. Correctly fitting orthotic footwear is paramount in preventing further damage to the Achilles tendon, recovering from the Achilles tendon injury and preventing the reoccurrence of Achilles tendon injury. Incorrect orthotic footwear can increase the likelihood of Achilles tendon injuries, delay recovery, and increase the chance of a reoccurrence.

An important aspect to the orthotic footwear is to correctly match the wearer's individual requirements such as shoe size, width, arch, cushioning, firmness, height, heel height, and location of the uprights relative to the anatomical ankle axis and calf midline. Typically an improper fit is identified by the uprights being too far forward or too far back relative to the midline of the patient's calf. It is desirable that one size can fit all. The problem is that not all legs and feet are the same. Further, during rehabilitation, a patient will require more than a single orthotic footwear device throughout a treatment plan, as heel wedges are adjusted according to the opinion of the medical practitioner and relocating the uprights becomes necessary to ensure alignment to the midline of the patient's calf.

Accordingly, there is a need to develop an orthotic foot device that can be adjusted to fit any number of sizes of feet and legs, in addition to being adjustable to any one patient during rehabilitation.

SUMMARY OF THE INVENTION

The present invention provides an orthotic foot device having a walking boot with at least one boot wall having at least one guide disposed along an anteroposterior direction of the boot wall, at least one upright bar disposed to attach to an individual's lower leg and disposed to translatably engage the at least one guide, at least one fastener that fixedly holds the at least one upright bar to the at least one guide when the at least one upright bar is desirably positioned.

According to one aspect of the invention, the walking boot further includes elements such as a rocker heel, a rocker forefoot, mid-sole rocker, heel rocker metatarsal padding, a modular heel pad, a modular arch support, a heel wedge, liner, an anterior shell, a posterior shell, a boot tread, a shin guard, a shin pad, an adjustable front foot strap, an adjustable heel strap and upright pads. Here, the rocker heel, mid-sole rocker and the rocker forefoot are a unitary element, where the rocker heel has a first curvature, the mid-sole rocker has a second curvature, and the rocker forefoot has a third curvature. Further, the heel wedge spans from a metatarsal region of a foot to at least a heal region of the foot, where the heel wedge has an angle in a range of 0 to 45 degrees relative to a base of the walking boot.

According to another aspect of the invention. The upright bar is disposed at an angle in a range between 0 to 90 degrees relative to a base of the walking boot.

In a further aspect of the invention, the at least one upright bar is positioned over the anatomical ankle axis and midline to a calf when the at least one fastener is secured.

In another aspect of the invention, the at least one guide disposed along the anteroposterior direction of the boot wall is at an angle between 0 to 90 degrees relative to a base of the walking boot.

According to another aspect of the invention, the at least one upright bar is attached to a rotatable connection disposed between the upright bar and the guide, wherein the rotatable connection translatable engages the guide.

In a further aspect, the upright bar is fixedly secured to the rotatable connection when positioned at a desired angle and the rotatable connection is fixedly secured to the guide when desirably positioned thereto.

According to another aspect of the invention, the at least one upright bar is attached to the guide disposed between a rotatable connection and the upright bar.

In a further aspect, the upright bar is fixedly secured to the guide when desirably positioned thereto and the rotatable connection is fixedly secured to the guide when the upright bar is positioned at a desired angle.

In yet another aspect of the invention, the guide comprises at least one slot formed in the at least one wall of the walking boot.

In one aspect of the invention, the guide includes at least one channel in the at least one wall of the walking boot, wherein the channel is disposed to receive an engagement element selected from the group consisting of a rolling element, a sliding element, an indexing element and a clamping element.

According to another aspect, the upright bar is disposed to attach to an individual's lower leg using an attachment element selected from the group consisting of a belt, a strap, a hook and pile connection, and a formed flexible material.

According to another aspect the upright bar includes at least one bar slot disposed to secure to said boot wall when a knee flexion angle is created.

BRIEF DESCRIPTION OF THE FIGURES

The objectives and advantages of the present invention will be understood by reading the following detailed description in conjunction with the drawing, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention.

Accordingly, the following preferred embodiment of the invention is set forth without any loss of generality to, and without imposing limitations upon, the claimed invention.

The present invention is an orthotic foot device with a sliding mechanism that includes uprights of the orthotic foot device that move with the leg to accommodate different heel wedges of different angles used throughout a treatment plan, where the sliding mechanism is secured in place after the uprights are properly adjusted. The application of replaceable heel wedges of differing angles is used to allow incremental stretching of the Achilles tendon, after an Achilles tendinopathy surgery. The application of the sliding mechanism provides proper anatomical support and aligns the uprights midline to the patient's calf each time a wedge angle is changed. The application of an adjustable upright improves the fit and function for the entire walking boot (or cam boot) orthopedic line of braces that are considered "off the shelf or non-custom." The adjustable sliding mechanism improves the fit to an "off the shelf" walking boot, which may be sized too big or too small. Typically an improper fit is identified by the uprights being too far forward or too far back relative to the midline of the patient's calf. The sliding uprights create adjustability for cam boots (or walking boots) to customize their fit, decrease bulk, decrease weight and improve compliance and fit. This feature is not limited to Achilles style walking boots. The sliding mechanisms primary function is to provide proper anatomical support and to align the uprights midline to the patient's calf.

Patients that benefit from the current invention vary greatly in diagnoses, especially patients who have had Achilles tendonopathies and acute Achilles tears. Further, the current invention provides cam boots (or walking boots) with a sliding mechanism to benefit patients diagnosed with hair line fractures of the foot and ankle, plantar fasciitis, diabetes, and other foot and ankle pathologies that require a cam boot. By providing an adjustable siding mechanism to these braces a patient benefit by improved compliance, which increases circulation, decreases healing time and improves patient outcomes.

Figure 1:
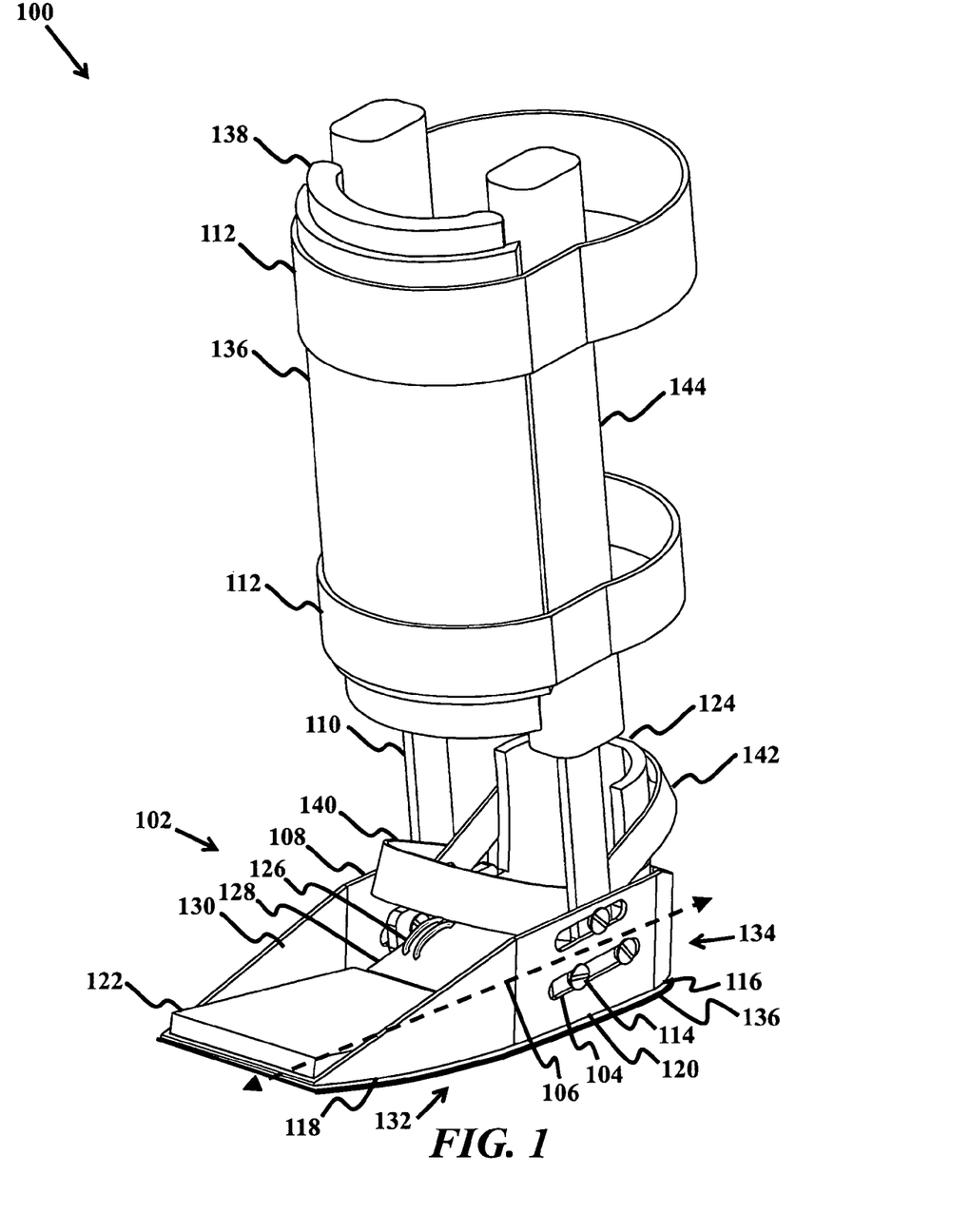
FIG. 1 shows a perspective view of an exemplary orthotic device with sliding uprights according to the present invention.

Referring to the figures, FIG. 1 shows a perspective view of an exemplary orthotic device with sliding uprights 100. As shown, a walking boot 102 with at least one boot wall 108 having at least one guide 104 disposed along an anteroposterior direction 106 of the boot wall 108, at least one upright bar 110 disposed to attach to an individual's lower leg using at least one leg attachment 112 and disposed to translatably engage the at least one guide 104, for example using at least one fastener 114 that fixedly holds the at least one upright bar 110 to the at least one guide 104 when the at least one upright bar 110 is desirably position along the guide 104 to match the anatomical ankle axis and calf midline of a patient. Further shown are elements of the invention that include a rocker heel 116, a rocker forefoot 118, a mid-sole rocker 120, a heel rocker metatarsal padding 122, a modular heel pad 124, a modular arch support 126, a heel wedge 128, liner 130, anterior shell 132, posterior shell 134 and a boot tread 136. According to the invention, the rocker heel 116, rocker forefoot 118, and mid-sole rocker 120 are a unitary element, where the rocker heel 116 has a first curvature, the mid-sole rocker 120 has a second curvature, and the rocker forefoot 118 has a third curvature (see FIG. 2). Further, the heel wedge 128 spans from a metatarsal region of a foot to at least a heal region of the foot, where the heel wedge 128 has an angle in a range of 0 to 45 degrees relative to a base of the walking boot (see FIG. 5). Further shown in FIG. 1, the invention includes a shin guard 136, a shin pad 138, an adjustable front foot strap 140, an adjustable heel strap 142 and upright pads 144. As shown, the upright bars 110 attach to an individual's lower leg using a leg attachment 112 such as a belt, a strap, a hook and pile connection, or a formed flexible material. Further, the leg attachments 112 are adjustable along the upright 110, or along the upright padding 140 using hook and pile or other attachments such as screws, adhesives, friction and the like.

Figure 2:
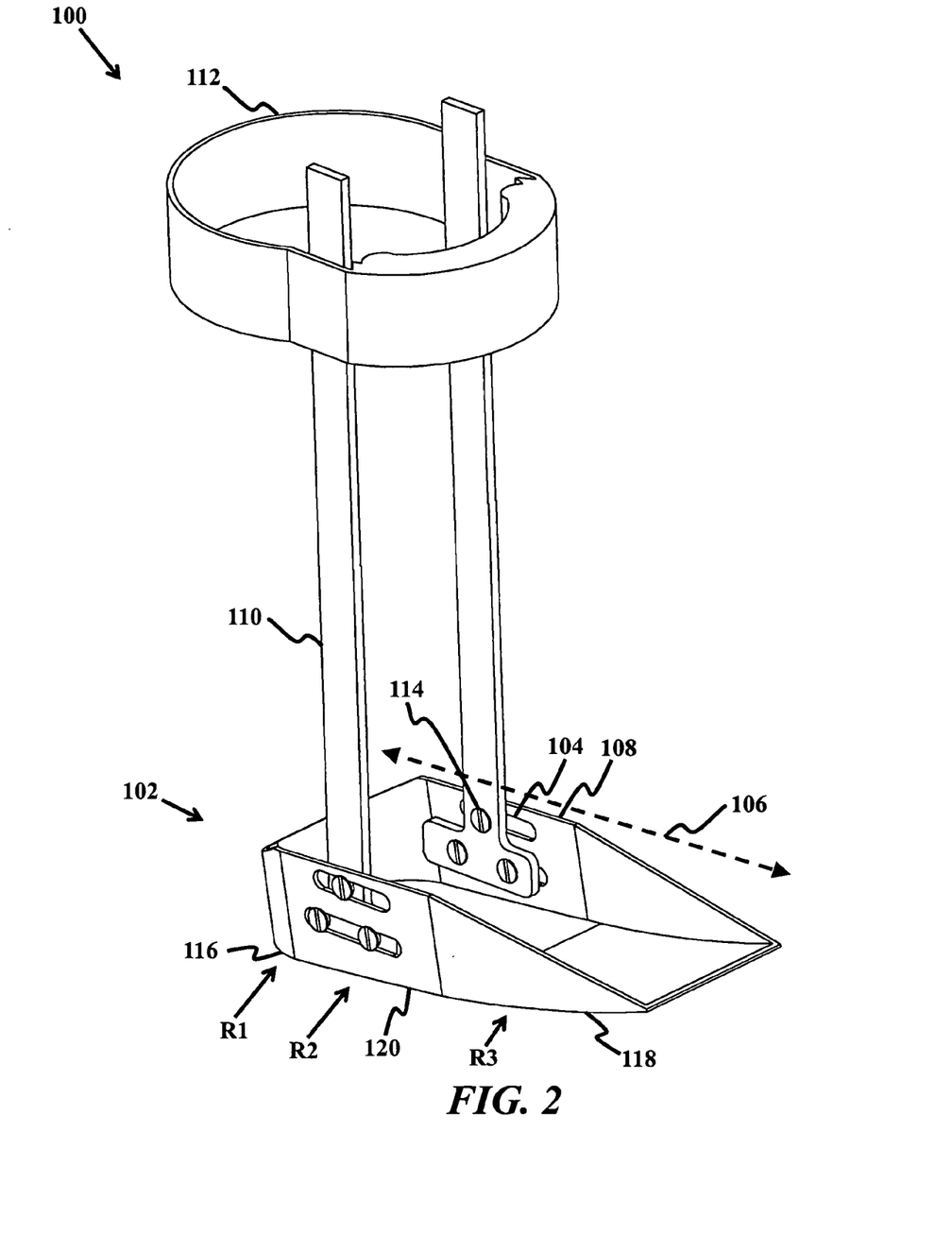
FIG. 2 shows a perspective view of exemplary key elements of an orthotic device with sliding uprights according to the present invention.

FIG. 2 shows a perspective view of exemplary key elements of an orthotic device with sliding uprights 100. As shown, a walking boot 102 with at least one boot wall having at least one guide 104 disposed along an anteroposterior direction 106 of the boot wall 108, at least one upright bar 110 disposed to attach to an individual's lower leg using leg attachments 112 and disposed to translatably engage the at least one guide 104 using a fastener 114. Further shown are the rocker heel 116 having a first curvature R1, the mid-sole rocker 120 having a second curvature R2, and the rocker forefoot 118 having a third curvature R3.

Figure 3:
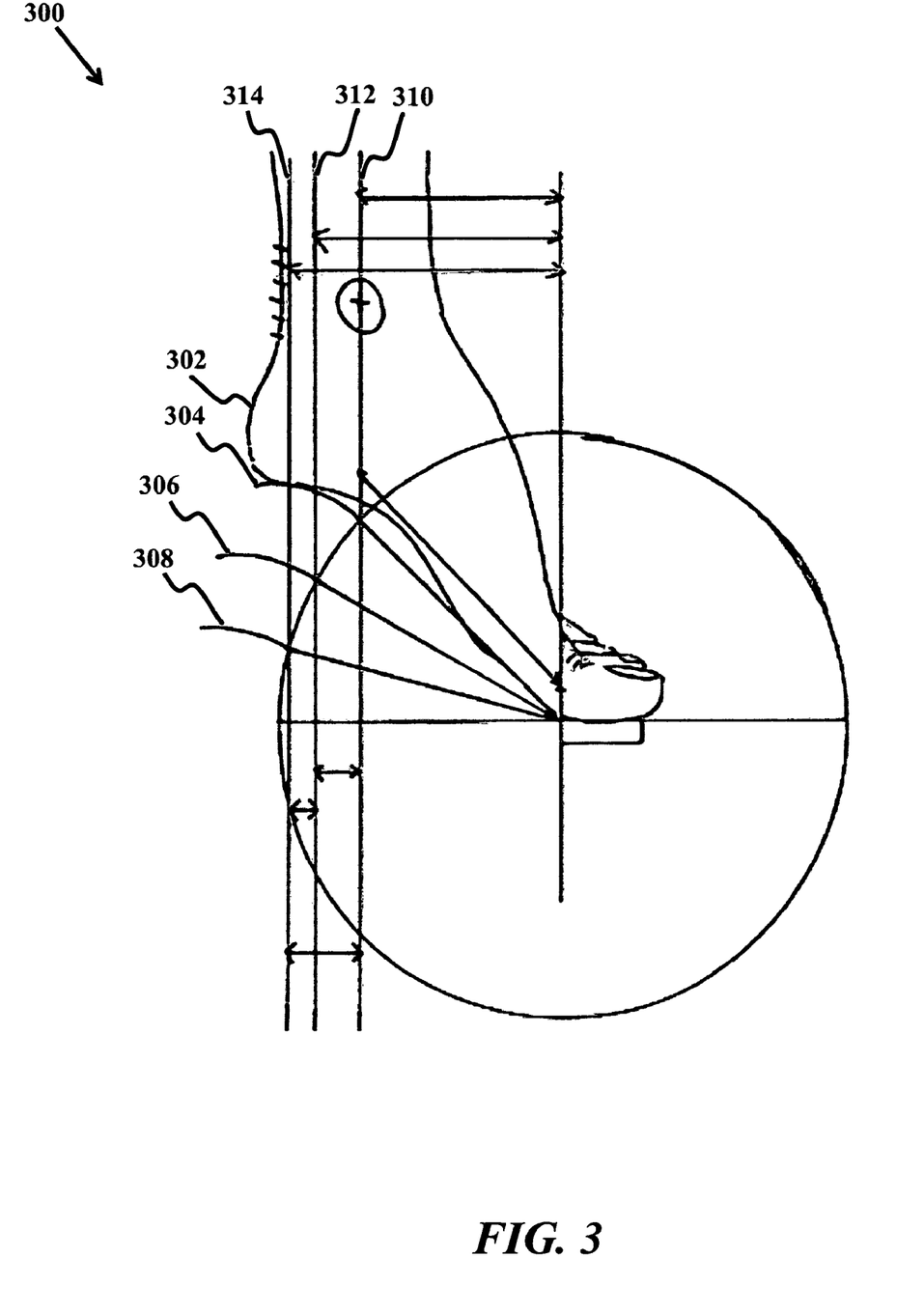
FIG. 3 shows a sketch of a treatment plan for an Achilles tendon patient according to the present invention.

FIG. 3 shows a sketch of a treatment plan 300 for an Achilles tendon patient. As shown, the patient's foot 302 is disposed in 3-positions: 45° (304), 30° (306), and 15° (308). FIG. 2, shows why the current invention is needed, where shown are respective calf midlines. Specifically, when the patient's foot is disposed at 45° (304) the corresponding calf midline is disposed at position 310, when the patient's foot is disposed at 30° (306) the corresponding calf midline is disposed at position 312, and when the patient's foot is disposed at 15° (308) the corresponding calf midline is disposed at position 314. In a treatment plan (see FIGS. 5a-5c) the calf moves posterior when a wedge is reduced in size or when a wedge is removed, thus the uprights 110 must also move posterior to maintain an anatomically correct fit over the ankle axis and calf midline. The current invention enables the three exemplary angles/positions to be addressed with a single orthotic foot device having a walking boot 100. Upright bar is positioned over the anatomical ankle axis and midline to a calf when the at least one fastener is secured. Here, the metatarsals are the center of rotation when each wedge (see FIGS. 5a-5c) is removed.

Figure 4:
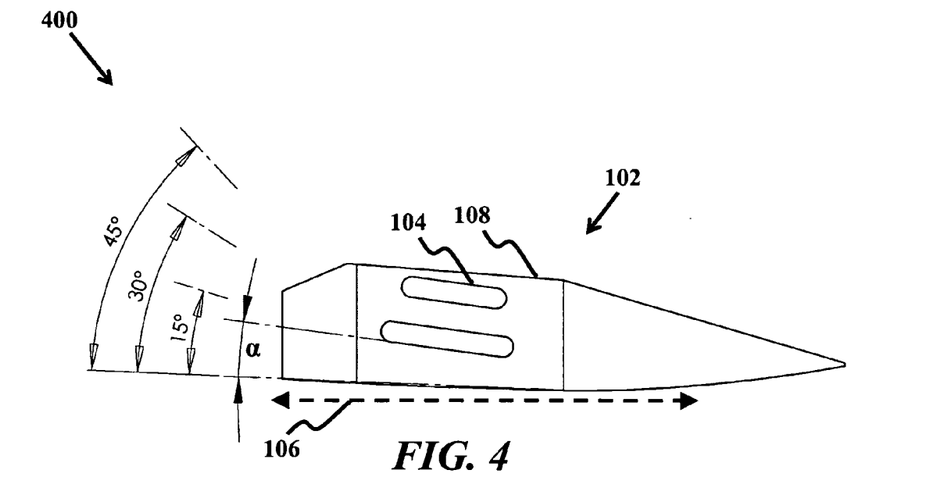
FIG. 4 shows a planar side view of the walking boot, according to the present invention.
Figure 5:
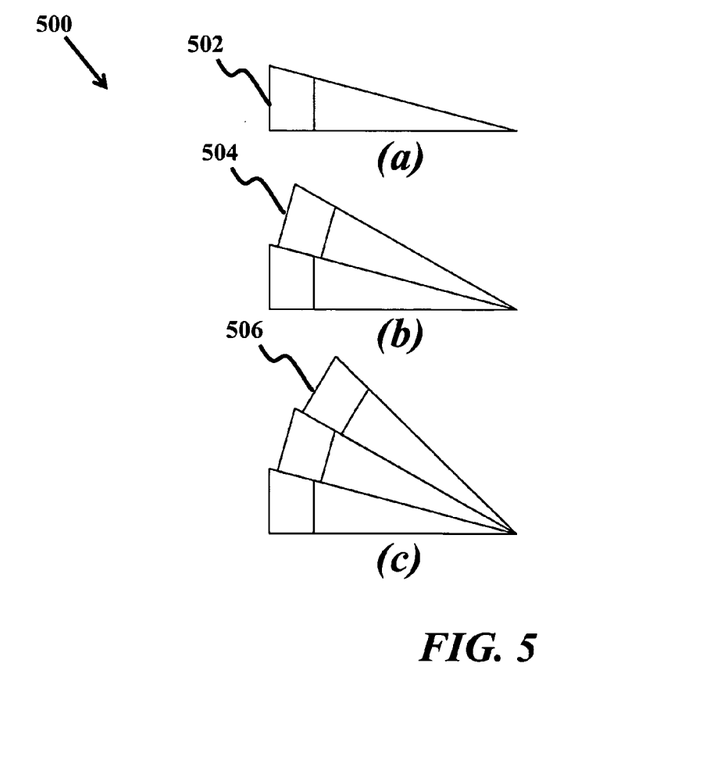
FIGS. 5a-5c show some exemplary wedge configurations of a treatment plan according to the present invention.

FIG. 4 shows a planar side view 400 of the walking boot 102, where shown are the guides 104 disposed along an anteroposterior direction 106 of the boot wall 108. As shown, the guide is disposed at an angle ($\alpha$) to create a knee flexion angle ($\beta$) (see FIG. 6) of the upright bar 110 disposed about perpendicular to the guide 104 to decrease an induced leg length discrepancy. According to the current invention, the angle ($\alpha$) can be an angle between 0° to 90° degrees relative to a base of the walking boot 102, where a preferred range is 5° to 15°, thus, the upright bar 110 when secured perpendicular to the span of the guide 104 and can be at an angle between 0° to 90° degrees relative to a base of the walking boot 102, where a preferred range is 5° to 15°.

FIGS. 5a-5c show some exemplary wedge configurations 500 of a treatment plan for a patient rehabilitating from an Achilles injury. Here FIG. 5a shows a wedge for positioning a foot at about a 15° (502), FIG. 5b shows a wedge for positioning a foot at about a 30° (504) and shows a wedge for positioning a foot at about a 45° (506), where it is understood that the wedge can be unitary or a plurality of wedges.

Figure 6:
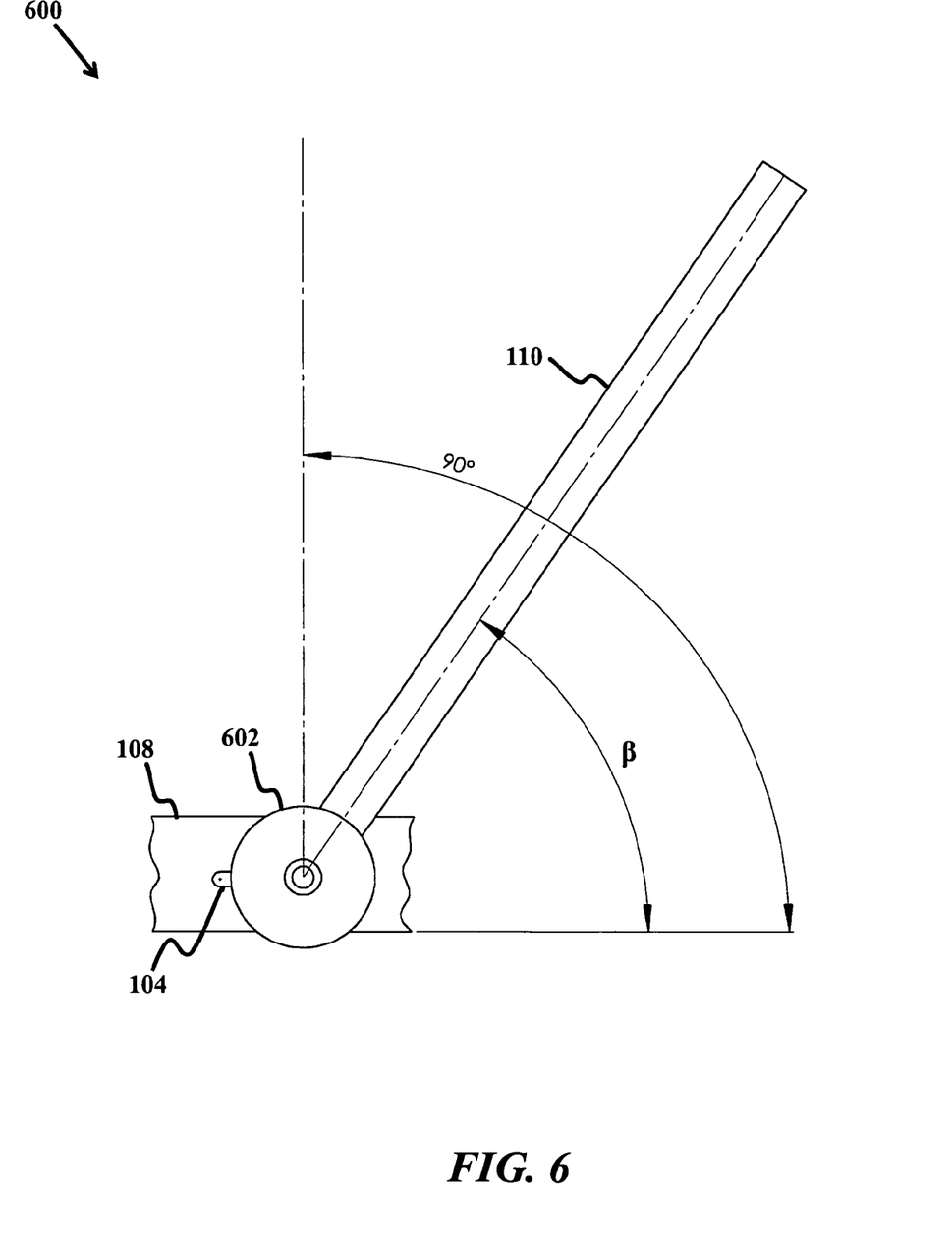
FIG. 6 shows a rotatable connection that is slideable along the guide according to the present invention.

FIG. 6 shows a rotatable connection embodiment 600 that is slideable along the guide 104. As shown, the at upright bar 110 is attached to a rotatable connection 602 that can be disposed on the outside of the rotatable bar or between the upright bar and the guide 104 in the boot wall 108, where the rotatable connection 602 translatably engages the guide. This embodiment of the invention allows the creation the knee flexion angle ($\beta$) of the upright bar 110, as mentioned earlier, when positioned at a desired angle and the rotatable connection 602 is fixedly secured to the guide 104. It should be apparent to one skilled in the art that the upright bar 110 can fixedly secured to the guide 104 when desirably positioned and the rotatable connection 602 can be fixedly secured to the guide 104 when the upright bar 110 is positioned at a desired angle ($\beta$).

It should be apparent to one skilled in the art that the guide 104 can include at least one channel in the at least one wall 108 of the walking boot 102, where the channel is disposed to receive an engagement element such as a rolling element, a sliding element, an indexing element and a clamping element.

Figure 7:
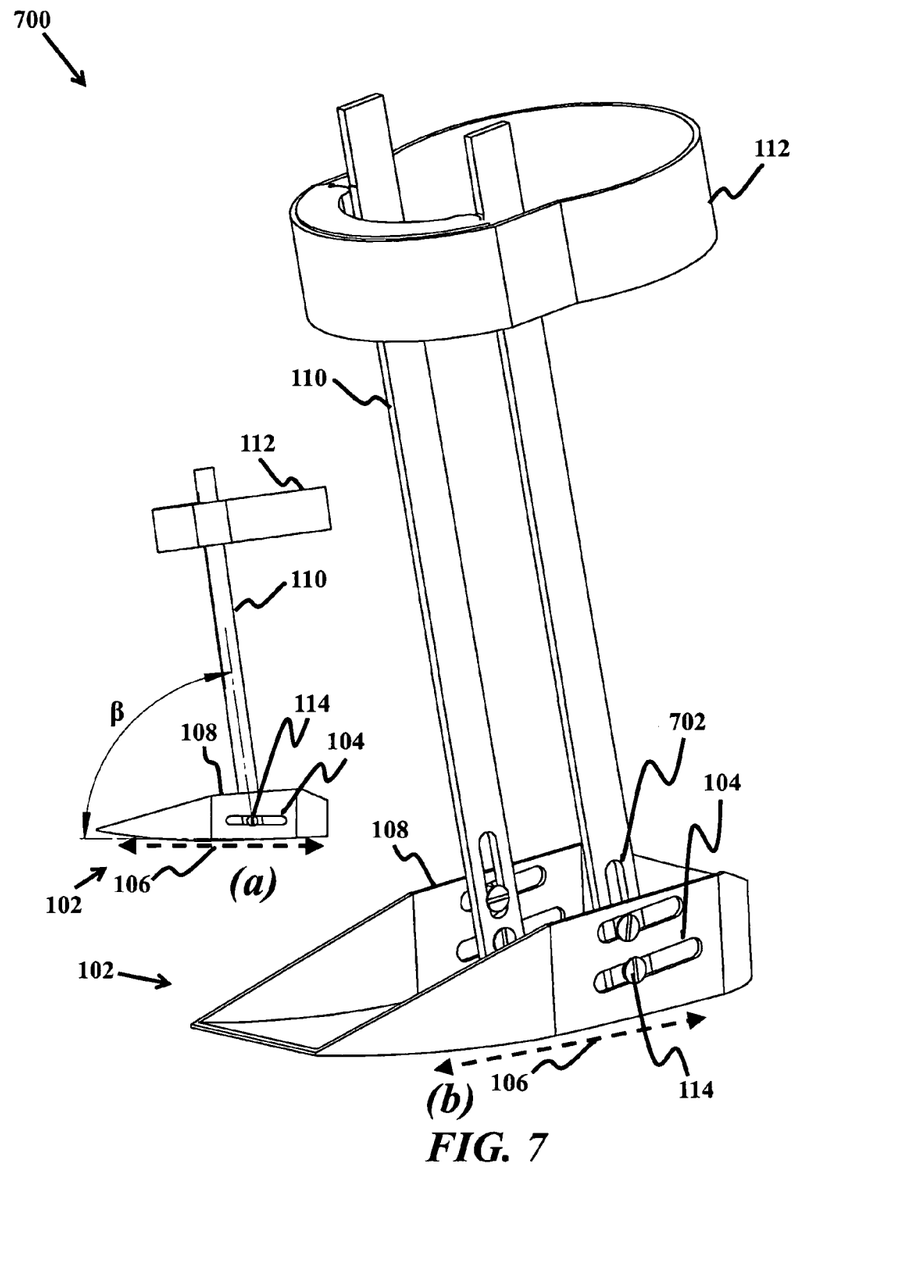
FIGS. 7a-7b a planar view and perspective view of the rotatable connection with the exemplary key elements of an orthotic device with sliding uprights according to the present invention.

FIGS. 7a-7b show a planar view a perspective view of the rotatable connection with the orthotic device 700. FIG. 7a shows the walking boot 102 having a single guide 104 disposed along an anteroposterior direction 106 of the boot wall 108. Here, the guide is disposed near horizontal, for example, with the base of the boot 102 and the upright bars 110 are disposed at an angle ($\beta$) to create a knee flexion angle. The upright bars 110 are secured to the guide 106 using a single fastener 114. According to the current invention, the upright bar 110 is disposed to attach to an individual's lower leg using the leg attachment 112 that translatably engages the guide 104 and is fixedly held in place when the upright bar 110 is desirably positioned. It should be evident to one skilled in the art that the number of guides 104 and fasteners 114 can be altered to many other arrangements such as two guides 104 and two fasteners 114 etc., without departing from the spirit of the current invention.

FIG. 7b shows the upright bar 110 having a bar slot 702 disposed along bar length and the walking boot 102 having two guides 104 disposed along an anteroposterior direction 106 of the boot wall 108. Here, the guides are disposed near horizontal, for example. Here the fastener 114 is disposed through the bar slot and through a first guide 104, while a second fastener is disposed a single hole in the upright bar 110 and a second guide 104. The upright bars 110 are secured to the guides 106 using a single fastener 114 for each guide 104. According to the current invention, the bar slot 702 along the upright bar 110 is disposed to enable the upright bars 110 to be desirably positioned, to create a knee flexion angle.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art.

All such variations are considered to be within the scope and spirit of the present invention as defined by the following claims and their legal equivalents.

What is claimed is:

1. An orthotic foot device comprising:
   a. a walking boot, wherein said walking boot comprises at least one boot wall having at least one linear guide disposed along an anteroposterior direction of said boot wall;
   b. at least one upright bar, wherein said at least one upright bar is disposed to attach to an individual's lower leg and disposed to translatably engage said at least one linear guide, wherein said translatable engagement comprises slidably positioning said at least one upright bar along said anteroposterior direction in said at least one linear guide of said boot wall; and
   c. at least one fastener, wherein said fastener fixedly holds said at least one upright bar to said at least one linear guide when said at least one upright bar is desirably positioned.

2. The orthotic foot device of claim 1, wherein said walking boot further comprises elements selected from the group consisting of a rocker heel, a rocker forefoot, mid-sole rocker, heel rocker metatarsal padding, a modular heel pad, a modular arch support, a heel wedge, liner, anterior shell, posterior shell, a boot tread, a shin guard, a shin pad, an adjustable front foot strap, an adjustable heel strap, and at least one upright pad.

3. The orthotic foot device of claim 2, wherein said rocker heel, said mid-sole rocker and said rocker forefoot are a unitary element, wherein said rocker heel has a first curvature said mid-sole rocker has a second curvature and said rocker forefoot has a third curvature.

4. The orthotic foot device of claim 2, wherein said heel wedge spans from a metatarsal region of a foot to at least a heal region of said foot, wherein said heel wedge has an angle in a range of 0 to 45 degrees relative to a base of said walking boot.

5. The orthotic foot device of claim 1, wherein said at least one upright bar is disposed at an angle in a range between 0 to 90 degrees relative to a base of said walking boot.

6. The orthotic foot device of claim 1, wherein said at least one upright bar is positioned over the anatomical ankle axis and midline to a calf when said at least one fastener is secured.

7. The orthotic foot device of claim 1, wherein said at least one guide disposed along said anteroposterior direction of said boot wall is at an angle between 0 to 90 degrees relative to a base of said walking boot.

8. The orthotic foot device of claim 1, wherein said at least one upright bar is attached to a rotatable connection disposed between said upright bar and said guide, wherein said rotatable connection translatably engages said guide.

9. The orthotic foot device of claim 1, wherein said upright bar is fixedly secured to a rotatable connection when positioned at a desired angle and said rotatable connection is fixedly secured to said guide when desirably positioned thereto.

10. The orthotic foot device of claim 1, wherein said at least one upright bar is attached to a rotatable connection, wherein said rotatable connection translatably engages said guide.

11. The orthotic foot device of claim 10, wherein said upright bar is fixedly secured to said guide when desirably positioned thereto and said rotatable connection is fixedly secured to said guide when said upright bar is positioned at a desired angle.

12. The orthotic foot device of claim 1, wherein said guide comprises at least one slot formed in said at least one wall of said walking boot.

13. The orthotic foot device of claim 1, wherein said guide comprises at least one channel in said at least one wall of said walking boot, wherein said channel is disposed to receive an engagement element selected from the group consisting of a rolling element, a sliding element, an indexing element and a clamping element.

14. The orthotic foot device of claim 1, wherein said upright bar is disposed to attach to an individual's lower leg using an attachment element selected from the group consisting of a belt, a strap, a hook and pile connection, and a formed flexible material.

15. The orthotic foot device of claim 1, wherein said upright bar comprises at least one bar slot disposed to secure to said boot wall when a knee flexion angle is created.

* * * * *